(12) United States Patent
Butler et al.

(10) Patent No.: US 6,589,726 B1
(45) Date of Patent: *Jul. 8, 2003

(54) METHOD AND APPARATUS FOR IN SITU SYNTHESIS ON A SOLID SUPPORT

(75) Inventors: John H. Butler, San Jose, CA (US); Thomas M. Brennan, San Francisco, CA (US)

(73) Assignee: Metrigen, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/645,021

(22) Filed: Aug. 23, 2000

Related U.S. Application Data

(63) Continuation-in-part of application No. 09/314,456, filed on May 18, 1999, now Pat. No. 6,210,894, which is a continuation of application No. 08/465,761, filed on Jun. 6, 1995, now Pat. No. 5,985,551, which is a continuation of application No. 08/068,540, filed on May 27, 1993, now Pat. No. 5,474,796, which is a continuation-in-part of application No. 07/754,614, filed on Sep. 4, 1991, now abandoned.

(51) Int. Cl.[7] .............................. C12Q 1/00; C12Q 1/68; C12M 1/34; G01N 33/552
(52) U.S. Cl. .......................... 435/4; 435/6; 435/287.1; 435/287.8; 436/518; 436/524; 436/527; 427/2.11; 427/2.13
(58) Field of Search ..................... 435/4, 6, 287.1, 435/287.8; 436/518, 524, 527; 427/2.11, 2.13

(56) References Cited

U.S. PATENT DOCUMENTS

| | | | |
|---|---|---|---|
| 3,736,042 A | 5/1973 | Markozits et al. ........... 359/398 |
| 4,705,705 A | 11/1987 | Bross ........................ 428/13 |
| 5,063,081 A | 11/1991 | Cozzette et al. ............... 435/4 |
| 5,143,854 A | 9/1992 | Pirrung et al. .............. 436/518 |
| 5,202,231 A | 4/1993 | Drmanac et al. ............... 435/6 |
| 5,252,743 A | 10/1993 | Barrett et al. ............. 548/303.7 |
| 5,412,087 A | 5/1995 | McGall et al. ............. 536/24.3 |
| 5,424,186 A | 6/1995 | Fodor et al. .................... 435/6 |
| 5,445,934 A | 8/1995 | Fodor et al. .................... 435/6 |
| 5,449,754 A | 9/1995 | Nishioka .................... 530/334 |
| 5,474,796 A | * 12/1995 | Brennan .................... 422/104 |
| 5,489,678 A | 2/1996 | Fodor et al. ............... 536/22.1 |
| 5,492,806 A | 2/1996 | Drmanac et al. ............... 435/5 |
| 5,510,270 A | 4/1996 | Fodor et al. ................ 436/518 |
| 5,525,464 A | 6/1996 | Drmanac et al. ............... 435/6 |
| 5,545,568 A | 8/1996 | Ellman ..................... 436/518 |
| 5,571,639 A | 11/1996 | Hubbell et al. ................ 430/5 |
| 5,614,608 A | 3/1997 | Krchnak et al. ............. 530/334 |
| 5,667,972 A | 9/1997 | Drmanac et al. ............... 435/6 |
| 5,679,773 A | 10/1997 | Holmes ..................... 530/334 |
| 5,695,940 A | 12/1997 | Drmanac et al. ............... 435/6 |
| 5,700,637 A | 12/1997 | Southern ..................... 435/6 |
| 5,700,642 A | 12/1997 | Monforte et al. ............... 435/6 |
| 5,739,386 A | 4/1998 | Holmes ..................... 562/437 |
| 5,744,305 A | 4/1998 | Fodor et al. .................... 435/6 |
| 5,800,992 A | 9/1998 | Fodor et al. .................... 435/6 |
| 5,830,655 A | 11/1998 | Monforte et al. ............... 435/6 |
| 5,837,832 A | 11/1998 | Chee et al. ................ 536/22.1 |
| 5,846,943 A | 12/1998 | Hindsgaul et al. ............. 514/25 |
| 5,856,104 A | 1/1999 | Chee et al. .................... 435/6 |
| 5,871,928 A | 2/1999 | Fodor et al. .................... 435/6 |
| 5,889,165 A | 3/1999 | Fodor et al. ................ 536/22.1 |
| 5,925,525 A | 7/1999 | Fodor et al. .................... 435/6 |
| 5,927,547 A | 7/1999 | Papen et al. .................. 222/57 |
| 5,968,740 A | 10/1999 | Fodor et al. .................... 435/6 |
| 5,972,619 A | 10/1999 | Drmanac et al. ............... 435/6 |
| 5,985,551 A | * 11/1999 | Brennan ....................... 435/6 |
| 6,018,041 A | 1/2000 | Drmanac et al. ........... 536/24.3 |
| 6,028,189 A | 2/2000 | Blanchard ................. 536/25.3 |
| 6,040,138 A | 3/2000 | Lockhart et al. ............... 435/6 |
| 6,054,270 A | 4/2000 | Southern ....................... 435/6 |
| 6,210,894 B1 | 4/2001 | Brennan ....................... 435/6 |

FOREIGN PATENT DOCUMENTS

| | | |
|---|---|---|
| EP | 161 058 A1 | 11/1985 |
| EP | 373203 | 8/1994 |
| WO | WO 89/10977 | 11/1989 |
| WO | WO 90/03382 | 4/1990 |
| WO | WO 90/15070 | 12/1990 |
| WO | WO 98/41531 | 11/1998 |

OTHER PUBLICATIONS

Andres, et al., "Transition–metal–mediated reactions in combinatorial synthesis," *Curr. Opin. Chem. Biol.* 2:353–362 (1998).

Atherton, et al., *Solid Phase Peptide Synthesis,* IRL press, London (1989).

Blanchard et al., "High Density oligonucleotide arrays," *Biosensors and Bioelectronics* 11:687–690 (1996).

Blixt, et al., "Solid–Phase Enzymatic Synthesis of a Sialyl Lewis X Tetrasaccharide on a Sepharose Matrix," *J. Org. Chem.* 63:2705–2710 (1998).

Brzoska, et al., "Evidence of a transition temperature for the optimum deposition of grafted monolayer coatings," *Nature* 360:719–721 (1992).

Case–Green, et al., "Analysing genetic information with DNA arrays," *Curr. Opin. In Chem. Biol.* 2:404–410 (1998).

Danishefsky, et al., "A Strategy for the Solid–Phase Synthesis of Oligosaccharides," *Science* 260:1307–1309 (1993).

DeRisi, J., et al., "Exploring the Metabolic and Genetic Control of Gene Expression on a Genomic Scale," *Science* 278:680–686 (1997).

(List continued on next page.)

Primary Examiner—Kenneth R. Horlick
Assistant Examiner—Alexander H. Spiegler
(74) Attorney, Agent, or Firm—Albert P. Halluin; Howrey, Simon, Arnold, & White, L.L.P.

(57) ABSTRACT

The present invention relates to methods for fabricating solid supports. More specifically, the present invention features methods for fabricating solid supports for in situ synthesis and for carrying out large numbers of reactions. The present invention also features solid supports with in situ synthesized long polynucleotides.

13 Claims, 5 Drawing Sheets

OTHER PUBLICATIONS

Drmanac, et al., "Accurate sequencing by hybridization for DNA diagnostics and individual genomics," *Nature Biotechnology* 16:54–58 (1998).

Duggan, D., et al., "Expression profiling using cDNA microarrays," *Nature Genetics Supplement* 21:10–14 (1999).

Forman, et al., "Thermodynamics of Duplex Formation and Mismatach Discrimination on Photolithographically Synthesized Oligonucleotide Arrays," Molecular Modeling of Nucleic Acids, Chapter 13, p. 221, American Chemical Society (1998).

Fruchtel, "Organic Chemistry on Solid Support," *Angew, Chem. Int. Ed. Engl* 35:17–42 (1996).

Giesen, et al., "A formula for thermal stability ($T_m$) prediction of PNA/DNA duplexes," *Nucleic Acids Research* 26(21):5004–5006 (1998).

Good, et al., "Antisense inhibition of gene expression in bacteria by PNA targeted to mRNA," *Nature Biotechnology* 16:355–358 (1998).

Gordon, et al., "Applications of Combinatorial Technologies to Drug Discover. 2. Combinatorial Organic Synthesis, Library Screening Strategies, and Future Directions," *J. Med. Chem.* 37:1385–1401 (1994).

Gururaja, et al., "Solid–phase synthesis of human salivary mucin–derived O–lined glycopeptides," *Lett. Pept. Sci.* 3:79–88 (1996).

Heckel, et al., "Oligosaccharide Synthesis on Controlled–Pore Glass as Solid Phase Material," *Synlett* 171–173 (1998).

Hermkens, et al., "Solid–Phase Organic Reactions: A Review of the Recent Literature," *Tetrahedron* 52(13):4527–4554 (1996).

Ito, et al., "Solid–Phase oligosaccharide synthesis and related technologies," *Curr. Opin. Chem. Biol.* 2:701–708 (1998).

Kahl, et al., "High–Yielding Method for On–Column Derivatization of Proteted Oligodeoxy–nucleotides and Its Application to the Convergent Synthesis of 5',3'–Bis conjugates," *J. of Org. Chem.* 63:4870–4871 (1998).

Kahl, et al., "Solution–Phase Bioconjugate Synthesis Using Protected Oligonucleotides Containing 3'–Alkyl Carboxylic Acids," *J. of Org. Chem.* 64:507–510 (1999).

Lipshultz, et al., "High density synthetic oligonucleotide arrays," *Nature Genetics Supplement* 21:20–24 (1999).

McDevitt, et al., "Glycosamino Acids: New Building Blocks for Combinatorial Synthesis," *J. Am. Chem. Soc.* 118:3818–3828 (1996).

McGall, et al., "The Efficiency of Light–Directed Synthesis of DNA Arrays on Glass Substrates," *J. Am. Chem. Soc.* 119:5081–5090 (1997).

McKenzie, S., et al., "Parallel molecular genetic analysis," *European Journal of Human Genetics* 6:417–429 (1998).

Meldal, et al., "Synthetic methods of glycopeptide assembly, and biological analysis of glycopeptide products," *Curr. Opin. Chem. Biol.* 1:552–563 (1997).

Merrifield, "Solid Phase Synthesis," *Science* 232:341–347 (1986).

Nicolaou, et al., "A General and Highly Efficient Solid Phase Synthesis of Oligosaccharides. Total Synthesis of a Heptasaccharide Phytoalexin Elicitor (HPE)," *J. Am. Chem. Soc.* 119:449–450 (1998).

Nielsen, "Applications of peptide nucleic acids," *Current Opinion in Biotechnology* 10:71–75 (1999).

Paulsen, et al., "New solid–phase oligosaccharide synthesis on glycopeptides bound to a solid phase," *J. Chem. Perkin Trans* 1:281–293 (1997).

Rademann, et al., "Repetitive Solid Phase Glycosylation on an Alkyl Thiol Polymer Leading to Sugar Oligomers Containing 1,2–trans– and 1,2–cis–Glycosidic Linkages," *J. Org. Chem.* 62:3650–3653 (1997).

Rodebaugh, et al., "Polymer–Supported Oligosaccharides via n–Pentenyl Glycosides: Methodology for a Carbohydrate Library," *J. Org. Chem.* 62:5660–5661 (1997).

Schena, et al., "Microarrays: biotechnology's discovery platform for functional genomics," *TIBTECH* 16:301–306 (1998).

Shuster, et al., "Solid–Phase Chemical–Enzymatic Synthesis of Glycopeptides and Oligosaccharides," *J. Am. Chem. Soc.* 116:1135–1136 (1994).

Singh–Gasson, et al., "Maskless fabrication of ligh–directed oligonucleotide microarrays using a digital micromirror array," *Nat. Biotech.* 17:974–978 (1999).

Thompson, et al., "Synthesis and Applications of Small Molecule Libraries," *Chem. Rev.* 96:555–600 (1996).

Toshima, et al., "Recent Progress in O–Glycosylation Methods and Its Application to Natural Products Synthesis," *Chem. Rev.* 93:1530–1531 (1993).

Venkatesan, et al., "Improved Utility of Photolabile Solid Phase Synthesis Supports for the Synthesis of Oligonucleotides Containing 3'–Hydroxyl Termini," *J. of Org. Chem.,* 61:525–529 (1996).

Verma, et al., "Modified Oligonucleotides: Synthesis and and Strategy for Users," *Annu. Rev. Biochem.* 67:99–134 (1998).

Wang, et al., "Large–Scale Identification, Mapping, and Genotyping of Single–Nucleotide Polymorphisms in the Human Genome," *Science* 280:1077–1082 (1998).

Yamada, et al., "An Efficient Synthesis of Sialoglycoconjugates on a Peptidase–Sensitive Polymer Support," *Tetrahedron Lett.* 36(52):9493–9496 (1995).

Yan, et al., "Glycosylation on the Merrifield Resin Using Anomeric Sulfoxides," *J. Am. Chem. Soc.* 116:6953–6954 (1994).

Zheng, et al., "Solid Support Oligosaccharide Synthesis: Construction of β–Linked Oligosacchgarides by Coupling of Glycal Derived Thioethyl Glycosyl Donors," *J. Org. Chem.* 63:1126–1130 (1998).

* cited by examiner

SEQUENCE LISTING

<160> NUMBER OF SEQ ID NOS: 10

<210> SEQ ID NO 1
<211> LENGTH: 10
<212> TYPE: DNA

```
<213> ORGANISM: Artificial sequence
<220> FEATURE:
<223> OTHER INFORMATION: Synthetic oligonucleotide

<400> SEQUENCE: 1
gatgctaccg                                                          10

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
gtcaagatgc taccgttcag                                               20

<210> SEQ ID NO 3
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 3
gactgactga                                                          10

<210> SEQ ID NO 4
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 4
tgactgactg actga                                                    15

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
ctgactgact gactgactga                                               20

<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 6
actgactgac tgactgactg actga                                         25

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 7
gactgactga ctgactgact gactgactga                                    30
```

-continued

```
<210> SEQ ID NO 8
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 8
tgactgactg actgactgac tgactgactg actga                                35

<210> SEQ ID NO 9
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 9
ctgactgact gactgactga ctgactgact gactgactga                           40

<210> SEQ ID NO 10
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 10
actgactgac tgactgactg actgactgac tgactgactg actga                     45
```

METHOD AND APPARATUS FOR IN SITU SYNTHESIS ON A SOLID SUPPORT

This application is a continuation-in-part application of U.S. patent application Ser. No. 09/314,456, filed on May 18, 1999 and issued as U.S. Pat. No. 6,210,894, which is a continuation application of U.S. patent application Ser. No. 08/465,761, filed on Jun. 6, 1995 and issued as U.S. Pat. No. 5,985,551, which is a continuation application of U.S. patent application Ser. No. 08/068,540, filed on May 27, 1993 and issued as U.S. Pat. No. 5,474,796, which is a continuation-in-part application of U.S. patent application Ser. No. 07/754,614, filed on Sep. 4, 1991, abandoned.

FIELD OF THE INVENTION

The present invention relates to methods for fabricating solid supports. More specifically, the present invention features methods for fabricating solid supports for in situ synthesis and for carrying out large numbers of reactions. The present invention also features solid supports with in situ synthesized long polynucleotides.

BACKGROUND OF THE INVENTION

Intense efforts are under way to map and sequence the human genome and the genomes of many other species. In June 2000, the Human Genome Project and biotech company Celera Genomics announced that a rough draft of the human genome has been completed. This information, however, will only represent a reference sequence of the human genome. The remaining task lies in the determination of sequence variations, such as mutations and polymorphism, which is important for the study, diagnosis, and treatment of genetic diseases.

In addition to the human genome, the mouse genome is also being sequenced. Genbank provides about 1.2% of the 3-billion-base mouse genome and a rough draft of the mouse genome is expected to be available by 2003 and a finished genome by 2005. The Drosophila Genome Project has also been completed recently.

During the past decade, the development of array-based hybridization technology has received great attention. This high throughput method, in which hundreds to thousands of polynucleotide probes immobilized on a solid surface are hybridized to target nucleic acids to gain sequence and function information, has brought economical incentives to many applications. See, e.g., McKenzie, S., et al., *European Journal of Human Genetics* 416–429 (1998), Green et al., *Curr.Opin. in Chem. Biol.* 2:404–410 (1998), Gerhold et al., *TIBS*, 24:168–173 (1999), and U.S. Pat. Nos. 5,700,637, 6,054,270, 5,837,832, 5,744,305, and 5,445,943.

One application is the monitoring of gene expression level and comparing of gene expression patterns. Many gene-specific polynucleotide probes derived from the 3' end of RNA transcripts are spotted on a solid surface. This array is then probed with fluorescently labeled cDNA representations of RNA pools from test and reference cells. The relative amount of transcript present in the pool is determined by the fluorescent signals generated and the level of gene expression is compared between the test and the reference cell. See, e.g., Duggan, D., et al., *Nature Genetics Supplement* 21:10–14 (1999), DeRisi, J., et al., *Science* 278:680–686 (1997), and U.S. Pat. Nos. 5,800,992, 5,871,928, and 6,040,138.

Another application of the array technology is the genotyping of mutations and polymorphisms, also known as re-sequencing. Typically, sets of polynucleotide probes, that differ by having A, T, C, or G substituted at or near the central position, are fabricated and immobilized on a solid support by in situ synthesis. Fluorescently labeled target nucleic acids containing the expected sequences will hybridize best to perfectly matched polynucleotide probes, whereas sequence variations will alter the hybridization pattern, thereby allowing the determination of mutations and polymorphic sites. See, e.g., Wang, D., et al., *Science* 280:1077–1082 (1998) and Lipshutz, R., et al., *Nature Genetics Supplement* 21:20–24 (1999), and U.S. Pat. Nos. 5,858,659, 5,856,104, 5,968,740, and 5,925,525.

Another application of the array technology is the de novo sequencing of target nucleic acids by polynucleotide hybridization. For example, an array of all possible 8-mer polynucleotide probes may be hybridized with fluorescently labeled target nucleic acids, generating large amounts of overlapping hybridization data. The reassembling of this data by computer algorithm can determine the sequence of target nucleic acids. See, e.g., Drmanac, S. et al., *Nature Biotechnology* 116:54–58 (1998), Drmanac, S. et al. *Genomics* 4:114–28 (1989), and U.S. Pat. Nos. 5,202,231, 5,492,806, 5,525,464, 5,667,972, 5,695,940, 5,972,619, 6,018,041, and 6,025,136.

In many applications of the array technology, polynucleotide probes are prepared by in situ synthesis on a solid support in a step-wise fashion. With each round of synthesis, nucleotide building blocks are added to growing chains until the desired sequence and length are achieved at each in situ synthesis site. In general, in situ polynucleotide synthesis on a solid support may be achieved by two general approaches.

First, photolithography may be used to synthesize polynucleotides on a solid support. Ultraviolet light may be shone through holes of a photolithograhic mask onto the support surface, which removes a photoactive protecting group, resulting in a 5' hydroxy group capable of reacting with another nucleoside. The mask therefore predetermines which nucleotides are activated. Successive rounds of deprotection and chemistry result in polynucleotides with increasing length. This method is disclosed in U.S. Pat. Nos. 5,143,854, 5,412,087, 5,445,934, 5,489,678, 5,571,639, 5,744,305, 5,837,832, 5,871,928, 5,889,165, and 6,040,138.

The second approach is the "drop-on-demand" method, which uses technology analogous to that employed in ink-jet printers (U.S. Pat. Nos. 5,985,551, 5,474,796, 5,700,637, 6,054,270, 6,028,189, 5,927,547, WO 98/41531, Blanchard et al., *Biosensors and Bioelectronics* 11:687–690 (1996), Schena et al., *TIBTECH* 16:301–306 (1998), Green et al., *Curr. Opin. Chem. Biol.* 2:404–410 (1998), and Singh-Gasson, et al., *Nat. Biotech.* 17:974–978 (1999)). This approach typically utilizes piezoelectric or other forms of propulsion to transfer reagents from miniature nozzles to solid surfaces. For example, a printer head may travel across the array, and at each spot, electric field contracts, forcing a microdroplet of reagents onto the array surface. Following washing and deprotection, the next cycle of polynucleotide synthesis is carried out.

The photolithography method used for in situ synthesis of polynucleotide probes presents many problems. First, the highest step yield reported for in situ photolithographic synthesis of polynucleotides is about 90% (Forman, J., et al., *Molecular Modeling of Nucleic Acids*, Chapter 13, p. 221, American Chemical Society (1998) and McGall et al., *J. Am. Chem. Soc.* 119:5081–5090 (1997)). In other words, when an additional nucleotide is added to each in situ synthesis site on a solid support, only about 90% of the products contain sequences with the additional nucleotide. The remaining 10% of the products are no longer available for nucleotide extension and remain as truncated sequences. The step yield of 90% is rather low for polynucleotide synthesis and is especially problematic for long polynucleotide synthesis. If one were to make polynucleotides of 50 nucleotides long with an average step yield of 90%, essentially none (only about 0.6%) on each in situ synthesis site would have the desired length of all 50 nucleotides. Essentially all polynucleotides (about 99.4%) would be truncated to some lesser number of nucleotides in length. If one were to make polynucleotides of 30 nucleotides long with an average step yield of 90%, less than about 5% of polynucleotides on each in situ synthesis site would have the desired length of 30 nucleotides and the rest (about 95%) being truncated sequences. Because truncated sequences do not correspond to the desired full length probe sequence, they may bind to unintended target nucleic acids and generate false hybridization signals. Therefore, the presence of large amounts of truncated polynucleotides inevitably leads to unpredictable hybridization performance.

Second, photolithographic synthesis of polynucleotides is expensive (e.g., the cost of masks). An array with N-mer polynucleotide probes may require 4×N photolithographic masks. For example, photolithographic synthesis of a 25-mer typically requires repeating the deprotection and coupling cycle about 100 times with about 100 different masks. To lower the cost per array, one has to synthesize large numbers of arrays with the same masks and probe sequences. In addition, changing the polynucleotide probe length and base composition in photolithography requires changing masks, which leads to high cost.

Finally, it is often necessary to introduce unnatural polynucleotide probes, for example, to balance the stability difference between A/T rich and G/C rich sequences, or to introduce a cleavage site. Incorporation of unnatural structures into the polynucleotide probes in the photolithography method involves new photodeprotection chemistry and will likely encounter even lower step yields and high redesigning cost. In addition, the photolithographic in situ synthesis method currently allows polynucleotide synthesis only in the 3' to 5' direction.

There is a need in the art to develop methods for fabricating solid supports for use in in situ synthesis of long polynucleotide probes with high efficiency and low cost. The present invention features the in situ synthesis of polynucleotides longer than 30 nucleotides. The present invention also features the in situ synthesis of polynucleotides longer than 15 nucleotides with greater purity. The average step yield is near or above 98%. The present synthesis method has many additional advantages as well, including low cost, flexibility in sequence and length designs, adaptivity to conventional solid-phase polynucleotide synthesis, and low chip-to-chip variability.

In addition to the use in polynucleotide synthesis, array fabrication methods in the present invention may also be used in in situ synthesis of other molecules including biopolymers such as polypeptides, polysaccharides, etc. The fabricated arrays may also be used as platforms for simultaneously carrying out large numbers of reactions, in particular, chemical and biological reactions. The present invention also features a method for reducing undesirable background signals in array-based applications.

SUMMARY OF THE INVENTION

The present invention features a method for fabricating a solid support comprising the steps of: (a) reacting a support surface with a first reagent to form a hydrophilic surface; (b) coating the support surface with a photoresist substance; (c) exposing selected regions of the support surface to light; (d) developing the support surface to form a patterned exposed surface and photoresist coated surface; (e) reacting the exposed surface with a second reagent to form hydrophobic sites; and (f) removing the photoresist coat from the photoresist coated surface.

The present invention also features a method for fabricating solid supports comprising the steps of: (a) reacting a support surface with a first reagent to form a hydrophobic surface; (b) coating the support surface with a photoresist substance; (c) exposing selected regions of the support surface to light; (d) developing the support surface to form a patterned exposed surface and photoresist coated surface; (e) removing the photoresist coat from the photoresist coated surface; and (f) reacting the exposed surface with a second reagent to form hydrophilic sites.

Any suitable solid supports may be used in the present invention. These materials include glass, silicon, wafer, polystyrene, polyethylene, polypropylene, polytetrafluorethylene, among others. Typically, the density of derivatized, hydrophilic or in situ synthesis sites on an array is between about 1–10,000 per $cm^2$, preferably below about 5,000, 1,000, 400, 200, 100, or 60 per $cm^2$. The area of each site may be about $0.1 \times 10^{-5}$ to $0.1\ cm^2$, preferably less than about 0.05, 0.01, or 0.005 $cm^2$. Typically, the total number of these sites on an array is between about 10–500,000, preferably, between about 10–100,000, 10–50,000, 10–10,000, 10–5000, 10–1000, 10–500, or 10–100. Synthesis reagents may be delivered using an ink-jet printing apparatus, such as a piezoelectric pump, a capillary tube, etc.

Fabricated solid supports may be further functionalized to provide covalent or noncovalent attachment to chemical or biological entities. In particular, fabricated/functionalized solid supports may be used in in situ synthesis of compounds, such as polynucleotides, polypeptides, or polysaccharides. Presynthesized compounds may also be deposited on these solid supports either covalently or non-covalently. Fabricated/functionalized solid supports may be employed as platforms for simultaneously carrying out large numbers of reactions. Any suitable unimolecular or non-unimolecular reaction (two or more reactants) may be applicable to the instant invention. For example, these reactions may involve cells, viruses, nucleic acids, proteins, peptides, carbohydrates, lipids, small molecules, etc. These reactions may be useful in the study, diagnosis, and treatment of genetic disorders, in genetic testing, in agriculture, in industrial use, etc.

The instant methods are particularly suited for in situ polynucleotide synthesis. It is possible to in situ synthesize polynucleotides of more than 15 nucleotides long with greater percentage of polynucleotides with the desired length at an in situ synthesis site. The average step yields are near or above about 98%. The present invention features solid supports comprising in situ synthesized polynucleotides wherein above about 5%, 10%, 15%, 20%, 25%, 30%, 35%, 40%, 45% or 50% of polynucleotides at an in situ synthesis site (e.g., hydrophilic sites) are longer than about 15, 20, 25, 30, 35, 40, 45, 50, 55, or 60 nucleotides long.

The present method also features a method for reducing background signals from an array comprising the sequential steps of: (a) derivatizing a solid support to form hydrophilic or hydrophobic sites; (b) coating said hydrophilic or hydrophobic sites with a photoresist substance; and (c) removing said photoresist substance. By removing the residual amount of photoresist, the present method also allows the reduction of background signals from the array surface in hybridization assays or other array applications.

DETAILED DESCRIPTION OF THE INVENTION

Figure 1A:
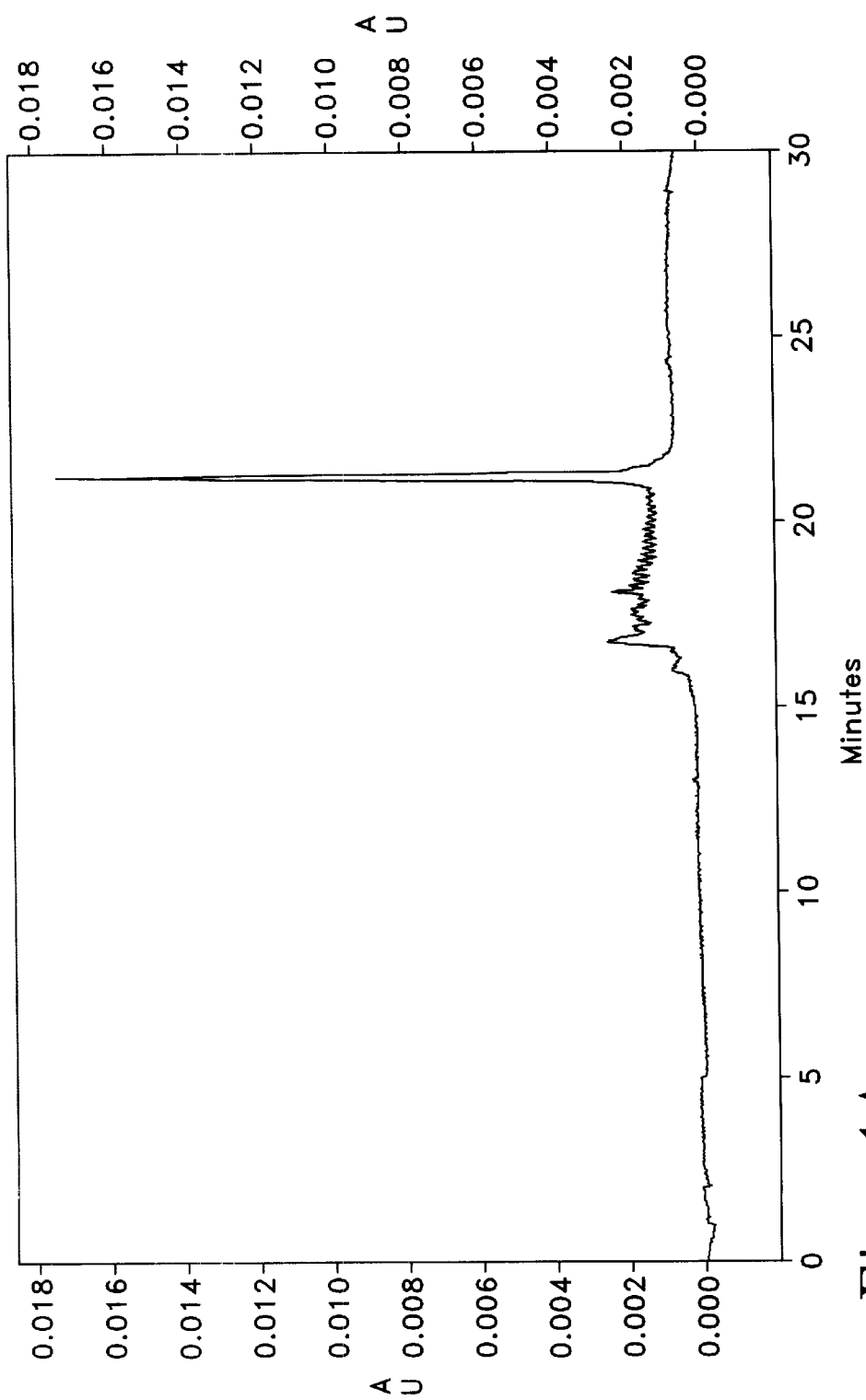
FIGS. 1A–C illustrates the electropherogram of cleavage products after 39 dT, dA or dC amidite couplings.

The present invention provides methods for fabricating a solid support for in situ synthesis. For example, the present invention allows the in situ synthesis of polynucleotides on a solid support. The present synthesis method allows the in situ synthesis of polynucleotides longer than 15 nucleotides with greater purity at in situ synthesis sites. In particular, the present synthesis method allows the in situ synthesis of polynucleotides longer than 30 nucleotides. The average step yield is near or above about 98%. The present synthesis method is economically feasible because of the flexible nature of its in situ polynucleotide synthesis compared to the photolithography technology. Array patterning and reagent delivery are generic processes, which are completely independent from the polynucleotide sequences at each site. The polynucleotide synthesis chemistry also uses standard rather than the custom synthesis reagents in photolithography. These advantages give complete design flexibility, with respect to the sequences and lengths of polynucleotides used in the array, the number and arrangement of array features, and the chemistry used to make array-immobilized polynucleotides.

In addition to the use in polynucleotide synthesis, array fabrication methods in the present invention may also be used in in situ synthesis of other molecules including biopolymers such as polypeptides, polysaccharides, etc. The fabricated arrays may also be used as platforms for simultaneously carrying out large numbers of reactions. In addition, the present invention features a method for reducing undesirable background signals in array-based applications.

Fabrication of Solid Supports

Any suitable solid supports (also known as arrays, chips, etc.) may be used in the present invention. These materials include glass, silicon, wafer, polystyrene, polyethylene, polypropylene, polytetrafluorethylene, among others. These materials typically have a rigid or semi-rigid surface. In some embodiments, at least one surface of the material is substantially flat. In some embodiments, these materials may contain features, such as wells, raised regions, etched trenches, etc. Solid supports are typically derivatized to provide covalent or noncovalent attachment to chemical or biological entities. Typically, the density of derivatized sites on an array is between about 1–10,000 per $cm^2$, preferably below about 5,000, 1,000, 400, 200, 100, or 60 per $cm_2$. The area of each site may be about $0.1 \times 10^{-5}$ to 0.1 $cm_2$, preferably less than about 0.05, 0.01, or 0.005 $cm^2$. Typically, the total number of derivatized sites on an array is between about 10–500,000, preferably, between about 10–100,000, 10–50,000, 10–10,000, 10–5000, 10–1000, 10–500, or 10–100. In situ synthesis may be performed on derivatized sites. Derivatized sites thus become in situ synthesis sites. The density of in situ synthesis sites on an array may be between about 1–10,000 per $cm^2$, preferably below about 5,000, 1,000, 400, 200, 100, or 60 per $cm^2$. The area of each site may be about $0.1 \times 10^{-5}$ to 0.1 $cm^2$, preferably less than about 0.05, 0.01, or 0.005 $cm^2$. Typically, the total number of in situ synthesis sites on an array is between about 10–500,000, preferably, between about 10–100,000, 10–50,000, 10–10,000, 10–5000, 10–1000, 10–500, or 10–100.

In some embodiments of the instant invention, surface tension arrays, which comprise patterned hydrophilic and hydrophobic sites, may be employed. A surface tension array may contain large numbers of hydrophilic sites against a hydrophobic matrix. A hydrophilic site typically includes free amino, hydroxyl, carboxyl, thiol, amido, halo, or sulfonate group, as well as modified forms thereof, such as activated or protected forms. A hydrophobic site is typically inert to conditions of in situ synthesis. For example, a hydrophobic site may include alkyl, fluoro group, as well as modified forms thereof, etc. In surface tension arrays, a hydrophilic site is spatially segregated from neighboring hydrophilic sites because of the hydrophobic sites between hydrophilic sites. This spatially addressable pattern enables the precise and reliable location of chemical or biological entities, such as molecules, cells, viruses, etc. The free amino, hydroxyl, carboxyl, thiol, amido, halo, or sulfonate group of the hydrophilic sites may then be covalently coupled with a linker moiety (e.g., polylysine, HEG, PEG, etc.) capable of supporting chemical and biological synthesis. The hydrophilic sites may also support non-covalent attachment to chemical or biological entities, such as molecules, cells, viruses, etc. Reagents delivered to the array are constrained by surface tension difference between hydrophilic and hydrophobic sites.

The surface tension array may also be appreciated from a thermodynamic perspective of wetting. Surface tension results from an imbalance of molecular forces in a liquid. At the surface of a liquid, the liquid molecules are attracted to each other and exert a net force pulling themselves together. High values of surface tension means that molecules tend to interact strongly. Lower values mean that molecules do not interact as strongly. Water has a very high value of surface tension because it has a high degree of hydrogen bonding. Organic molecules with polar groups such as hydroxyl, carboxyl or cyano have a slightly lower surface energy than water. Pure hydrocarbons are even lower, while fluorinated compounds are very low, because the fluorine atom does not share electrons very well so only dispersion interactions (entropy of mixing) occur.

Molecules in a liquid state experience strong intermolecular attractive forces. These cohesive forces between liquid molecules are responsible for the phenomenon known as surface tension. Molecules at the surface of a liquid droplet do not have other like molecules, and as a consequence cohere more strongly with adjacent molecules which are directly associated them.

When the attractive forces are between unlike molecules, they are described as adhesive forces. The adhesive force between a water molecule and the wall of a glass capillary (i.e., the SiOH group) is stronger than the cohesive force between two water molecules at the surface. The effect of this imbalance between adhesion and cohesion is that the meniscus will turn upward and contribute to capillary action. Conversely, for mercury, the cohesive force between two mercury atoms is stronger than the adhesive force between mercury and glass, and the meniscus turns down at the wall.

When a liquid is in contact with a solid surface, the contact angle θ may be used to quantitatively measure the extent of this interaction.

$$\gamma_{SV} - \gamma_{SL} = \gamma_{LV} \cos \theta$$

where $\gamma_{SV}$ is the surface free energy of the solid, $\gamma_{SL}$ is the interfacial free energy between the solid and the liquid, $\gamma_{LV}$ is the surface free energy of the liquid.

When a droplet of liquid is in contact with a surface which is patterned into two regions which have different surface energies, then there is a net attraction of the liquid into the region of higher surface energy. The droplet may move, as a result of the difference in surface tension between the two regions.

In other words, polar liquids wet polar surfaces in preference to nonpolar surfaces. For a patterned array where the polar synthesis regions (hydrophilic sites) are separated by nonpolar regions (hydrophobic sites), droplets of liquid are confined to a particular synthesis site, and will not migrate to an adjacent site because of the surface tension difference imposed by the nonpolar mask.

For surface tension arrays, hydrophilic sites are derivarized sites. The density of hydrophilic sites on an array is typically between about 1–10,000 per cm$^2$, preferably below about 5,000, 1,000, 400, 200, 100, or 60 per cm$^2$. The area of each site may be about 0.1×10$^{-5}$ to 0.1 cm$^2$, preferably less than about 0.05, 0.01, or 0.005 cm$^2$. Typically, the total number of hydrophilic sites on an array is between about 10–500,000, preferably, between about 10–100,000, 10–50,000, 10–10,000, 10–5000, 10–1000, 10–500, or 10–100.

A number of methods for fabricating surface tension arrays have been described in U.S. Pat. Nos. 5,985,551 and 5,474,796. One of such methods involves coating a solid surface with a photoresist substance and then using a generic photomask to define the array patterns by exposing them to light. The exposed surface may then be reacted with a suitable reagent to form a stable hydrophobic matrix. For example, fluoroalkylsilane or long chain alkylsilane, such as octadecylsilane, may be employed to form a hydrophobic matrix. The remaining photoresist substance may then be removed and the solid support may react with a suitable reagent, such as aminoalkyl silane or hydroxyalkyl silane, to form hydrophilic regions.

In the present method of array fabrication, the solid support may be first reacted with a suitable derivatizing reagent to form a hydrophobic surface. For example, the hydrophobic surface may be derivatized by vapor or liquid treatment of fluoroalkylsiloxane or alkylsilane. The hydrophobic surface may then be coated with a photoresist substance, photopatterned and developed. The exposed hydrophobic surface may be reacted with suitable derivatizing reagents to form hydrophilic sites. For example, the exposed hydrophobic surface may be removed by wet or dry etch such as oxygen plasma and then derivatized by aminoalkylsilane or hydroxylalkylsilane treatment to form hydrophilic sites. The photoresist coat may be removed to expose the underlying hydrophobic sites. The hydrophilic sites may be further functionalized, if necessary, for anchoring in situ synthesis or for depositing chemical or biological entities.

Alternatively, the solid support may be first reacted with a suitable derivatizing reagent to form a hydrophilic surface. For example, the hydrophilic surface may be derivatized by vapor or liquid treatment of aminoalkylsilane or hydroxylalkylsilane. The derivatized surface may then be coated with a photoresist substance, photopatterned, and developed. The exposed surface may be reacted with suitable derivatizing reagents to form hydrophobic sites. For example, the hydrophobic sites may be formed by fluoroalkylsiloxane or alkylsilane treatment. The photoresist coat may be removed to expose the underlying hydrophilic sites. The hydrophilic sites may be further functionalized, if necessary, for anchoring in situ synthesis or for depositing chemical or biological entities.

Variations of these procedures may also be used to fabricate a solid support surface such that solution of reactants at a derivatized site is spatially separated from solution of reactants at other derivatized sites by surface tension. Separate reactions may be carried out at each derivatized site.

The advantages of the instant methods are (1) the photoresist acts as a physical barrier separating the hydrophilic and hydrophobic derivatization processes and inhibits any cross derivatization between the two processes and (2) there is no photoresist residue present on the array surface prior to derivatization. By using the instant array fabrication methods, the undesirable coupling between photoresist and derivatizing reagent is minimized and the resulting solid support is more uniform with respect to derivatization, in situ synthesis, and array applications. This method thus allows more control of photopatterning, eliminates batch to batch variability, and increases the step yields of in situ synthesis.

The present invention features a solid support with in situ synthesized long polynucleotides (more than about 15 nucleotides long) with average step yields near or above about 98%. At an in situ synthesis site (e.g., hydrophilic sites), above about 5%, 10%, 15%, 20%, 25%, 30%, 35%, 40%, 45% or 50% of polynucleotides are longer than about 15, 20, 25, 30, 35, 40, 45, 50, 55, or 60 nucleotides long. The percentage of long polynucleotides at an in situ synthesis site may be obtained using any methods known to those skilled in the art. For example, percentage of long polynucleotides may be obtained by calculating the average step yield (also known as coupling yield) of in situ synthesis. As an example, if the average step yield at an in situ synthesis sites is estimated to be 98% in the synthesis of polynucleotides of 20 nucleotides long, about 68% of polynucleotides at the in situ synthesis site are of 20 nucleotides long (0.98$^{20}$=0.68). The calculation or estimation of average step yields of in situ polynucleotide synthesis is also known to those skilled in the art (see, e.g., Forman, J., et al., *Molecular Modeling of Nucleic Acids*, Chapter 13, p. 221, American Chemical Society (1998)). For example, the step yields may be calculated or estimated by hybridization assays, chromatography, eletrophoresis, etc. In some embodiments, in situ synthesized polynucleotides may be cleaved from the solid support to obtain the percentage of long polynucleotides at an in situ synthesis site. For example, in situ synthesized polynucleotides may be cleaved from the solid support followed by chromatography of polynucleotides of selected length.

In addition to the synthesis of long polynucleotides, the present method also allows the reduction of background signals from the array surface in hybridization assays or other array applications by removing the residual amount of photoresist.

Photoresist substances are readily known to those of skill in the art. For example, an optical positive photoresist substance (e.g., AZ 1350 (Novolac™ type-Hoechst Celanese™) (Novolac™ is a proprietary novolak resin, which is the reaction product of phenols with formaldehyde in an acid condensation medium)) or an E-beam positive photoresist substance (e.g., EB-9 (polymethacrylate by Hoya™)) can be used.

Suitable hydrophilic and hydrophobic derivatizing reagents are also well known in the art. Preferably, fluoroalkylsilane or alkylsilane may be employed to form a hydrophobic surface and aminoalkyl silane or hydroxyalkyl silane may be used to form hydrophilic sites. As an example, a number of siloxane derivatizing reagents are listed below:
1. Hydroxyalkyl siloxanes (Silylate surface, functionalize with diborane, and $H_2O_2$ to oxidize the alcohol)
    a. allyl trichlorochlorosilane→→3-hydroxypropyl
    b. 7-oct-1-enyl trichlorochlorosilane→→8-hydroxyoctyl
2. Diol (bis-hydroxyalkyl) siloxanes (silylate surface, and hydrolyze to diol)
    a. glycidyl trimethoxysilane→→(2,3-dihydroxypropyloxy)propyl
3. Aminoalkyl siloxanes (amines require no intermediate functionalizing step)
    a. 3-aminopropyl trimethoxysilane→3-aminopropyl
4. Dimeric secondary aminoalkyl siloxanes
    a. bis (3-trimethoxysilylpropyl) amine→bis(silyloxylpropyl)amine Glass (polytetrasiloxane) is particularly suitable for surface tension arrays, because of the numerous techniques developed by the semiconductor industry using thick films (1–5 microns) of photoresists to generate masked patterns of exposed glass surfaces. After sufficient cleaning, such as by treatment with $O_2$ radical (e.g., using an $O_2$ plasma etch, ozone plasma treatment, etc.) followed by acid wash, the glass surface may be derivatized with a suitable reagent to form a hydrophilic surface. Suitable reagents may include aminoalkyl silane, hydroxyalkyl silane, among others. In particular, glass surface may be uniformly aminosilylated with an aminosilane, such as aminobutyldimethylmethoxysilane (DMABS). The derivatized surface may then be coated with a photoresist substance, soft-baked, photopatterned using a generic photomask to define the array patterns by exposing them to light, and developed. The underlying hydrophilic sites are thus exposed in the mask area and ready to be derivatized again to form hydrophobic sites, while the photoresist covering region protects the underlying hydrophilic sites from further derivatization. Suitable reagents, such as fluoroalkylsilane or long chain alkylsilane, may be employed to form hydrophobic sites. For example, the exposed hydrophilic sites may be burned out with an $O_2$ plasma etch. The exposed regions may then be fluorosilylated. Following the hydrophobic derivatization, the remaining photoresist can be removed, for example by dissolution in warm organic solvents such as methyl isobutyl ketone or N-methyl pyrrolidone (NMP), to expose the hydrophilic sites of the glass surface. For example, the remaining photoresist may be dissolved off with sonication in acetone and then washed off in hot NMP.

A number of organic polymers also have desirable characteristics for surface tension arrays. For example, Teflon (polytetrafluoroethylene) may be used. Patterned derivatization of this type of material may be accomplished by reactive ion or plasma etching through a physical mask or using an electron beam, followed by reduction to surface hydroxymethyl groups. Polypropylene/polyethylene may be surface derivatized by gamma irradiation or chromic acid oxidation, and converted to hydroxy or aminomethylated surfaces. Highly crosslinked polystryene-divinylbenzene (ca. 50%) is non-swellable, and may be readily surface derivatized by chloromethlylation and subsequently converted to other functional groups. Nylon provides an initial surface of hexylamino groups, which are directly active. The hydrophobic patterning of these surfaces may be effected using the same type of solution based thin film masking techniques and gas phase derivatization as glass, or by direct photochemical patterning using o-nitrobenzylcarbonyl blocking groups. Perfluoroalkyl carboxylic and sulfonic acid derivatives are now used to provide the hydrophobic mask of the underlying surface. Subsequent to the patterning of these surfaces, suitable linker moieties may be coupled to the reactive group such as the hydroxy or amino group.

In addition to the use of photoresist in generating patterned hydrophilic and hydrophobic sites, surface tension arrays may be fabricated without the use of photoresist. For example, a solid support may be first reacted with a reagent to form hydrophilic sites. The hydrophilic sites may then be reacted in selected areas. The remaining hydrophilic sites may then be reacted with a reagent to form hydrophobic sites. The protected hydrophilic sites may then be deprotected to anchor in situ synthesis or to deposit chemical or biological entities. For example, a glass surface may be first reacted with a reagent to generate free hydroxyl or amino sites. These hydrophilic sites may be reacted with a protected nucleoside coupling reagent or a linker to protect selected hydroxyl or amino sites. A protected nucleotide coupling reagent includes, for example, a DMT-protected nucleoside phosphoramidite, DMT-protected H-phosphonate, etc. A linker may be of six or more atoms in length. The unprotected hydroxyl or amino sites may then be reacted with a reagent, for example, perfluoroalkanoyl halide, to form hydrophobic sites inert to in situ polynucleotide synthesis. The protected hydrophilic sites may be deprotected to anchor in situ polynucleotide synthesis. Variations of these procedures may also be used to fabricate a solid support surface such that solution of chemical or biological entities at a derivatized site is spatially separated from solutions of chemical or biological entities at other derivatized sites.

In Situ Synthesis or Spotting of Presynthesized Compounds

Solutions of reactants may be added to hydrophilic sites on the surface using the "drop-on-demand" method, which is analogous to the ink-jet printing technology. This approach typically utilizes piezoelectric or other forms of propulsion to transfer reagents from miniature nozzles to solid surfaces. For example, a printer head may travel across the array, and at each spot, electric field contracts, forcing a microdroplet of reagents onto the array surface. The drop-on-demand technology allows high-density gridding of virtually any reagents of interest. It is also easier using this method to take advantage of the extensive chemistries already developed for polynucleotide synthesis, for example, flexibility in sequence designs, synthesis of polynucleotide analogs, synthesis in the 5'-3' direction, etc. Because ink jet technology does not require direct surface contact, piezoelectric delivery is amendable to very high throughput.

A piezoelectric pump may be used to add reagents to the in situ synthesis. Microdroplets of 50 picoliters to 2 microliters of reagents may be delivered to the array surface. The design, construction, and mechanism of a piezoelectric pump are described in U.S. Pat. Nos. 4,747,796 and 5,985,551. The piezoelectric pump may deliver minute droplets of liquid to a surface in a very precise manner. For example, a picopump is capable of producing picoliters of reagents at up to 10,000 Hz and accurately hits a 250 micron target at a distance of 2 cm.

The reactions at the hydrophilic sites may form covalent bonds such as esters or amide bonds or may involve non-covalent specific binding reactions such as antibody/antigen binding or base pairing. In some embodiments, the growing polynucleotides are attached to the solid support via an intervening linker moiety. The linker moiety may be of six or more atoms in length. Convention solid phase polynucleotide synthesis is well known in the art of polynucleotide synthesis. See, e.g., Protocols for Oligonucletides and Analogs; Agrawal, S., Ed.; Hurnana Press: Totowa, N.J., (1993). As used in the instant invention, the terms polynucleotides/nucleotides (often referred to as oligonucleotides, primers, probes, nucleic acids, etc) refer to naturally occurring polynucleotides/nucleotides, e.g., DNA or RNA. These terms also refer to modified/protected forms thereof or analogs of naturally occurring polynucleotides. The synthesis of many modified or unnatural polynucleotides is well known in the art. See, e.g., Verma et al., *Annu. Rev. Biochem.* 67:99–134 (1998), Venkatesan et al. *J. of Org. Chem.*, 61:525–529 (1996), Kahl et al., *J. of Org. Chem.*, 64:507–510 (1999), and Kahl et al., *J. of Org. Chem.* 63:4870–4871 (1998), and U.S. Pat. Nos. 5,739,386, 5,700,642 and 5,830,655. The modification of polynucleotides may be located at polynucleotide bases, sugars or backbone. For example, polynucleotides containing a modified 3'-5' internucleotide linkage in place of one of the phosphodiester groups, such as ribose, dialkoxysilane, phosphorothioate, and phosphoramidate internucleotide linkage may be synthesized. In addition, the naturally occurring nucleic acids have 3'-5' phosphodiester linkage may be replaced with 2'-5' linkage.

The highly charged phosphodiesters in natural nucleic acid backbone may be replaced by neutral sugar phosphate backbone analogues. For example, phosphotriesters in which the oxygen that is normally charged in natural nucleic acids is esterified with an alkyl group may be used. Another class of backbone analogs is polypeptide nucleic acids (PNAs), in which a peptide backbone is used to replace the phosphodiester backbone. PNAs are capable of forming sequence-specific duplexes that mimic the properties of double-strand DNA except that the complexes are completely uncharged. See, e.g., Giesen, U. et al., *Nucleic Acids Research* 26(21):5004–5006 (1998); Good, L., et al., *Nature Biotechnology* 16:355–358 (1998); and Nielsen, P., *Current Opinion in Biotechnology* 10:71–75 (1999).

Modifications of bases and sugars may include a substituent on or replacement of one of the bases or sugars, such as 7-deazaguanosine, 5-methylcytosine, 2,6-diamino purine, 5-bromouridine, 5-Chlorouridine, inosine, uridine, and the like.

In some embodiments, the modified polynucleotides may contain a cleavage site. The cleavage methods may include a variety of enzymatic, or non-enzymatic means, such as chemical, thermal, photolytic cleavage, or a combination thereof. For example, the polynucleotides may include a photocleavable linker, such as orthonitrobenzyl class of photocleavable linkers. The cleavable sites contained within the modified polynucleotides may include chemically cleavable groups, such as dialkoxysilane, 3'-(S)-phosphorothioate, 5'-(S)-phosphorothioate, 3'-(N)-phosphoramidate, 5'-(N)-phosphoramidate, and ribose.

It will be appreciated by one of skill in the art that the immobilized polynucleotides may be tagged with detectable labels. Detectable labels include any composition detectable by spectroscopic, photochemical, biochemical, immunochemical, electrical, optical or chemical means. Useful labels may include biotin for staining with labeled streptavidin conjugate, magnetic beads (e.g., Dynabeads™), fluorescent molecules (e.g., fluorescein, texas red, rhodamine, green fluorescent protein, FAM, JOE, TAMRA, ROX, HEX, TET, Cy3, C3.5, Cy5, Cy5.5, IRD41, BODIPY and the like), radiolabels (e.g., $^3$H, 251I, $^{35}$S, $^{34}$S, $^{14}$C, $^{32}$P, or $^{33}$P), enzymes (e.g., horse radish peroxidase, alkaline phosphatase and others commonly used in an ELISA), colorimetric labels such as colloidal gold or colored glass or plastic (e.g., polystyrene, polypropylene, latex, etc.) beads, mono and polyfunctional intercalator compounds.

In addition to polynucleotide synthesis, the fabricated arrays may also be used in other biopolymer synthesis, such as polypeptides, polysaccharides or modified forms thereof. Methods for solid phase synthesis of large combinatorial peptide libraries have been described in the literature (Merrifield, *Science* 232:342–347 (1986), Atherton et al., *Solid Phase Peptide Synthesis*, IRL press, London (1989), Albericio et al., *Methods Enzymol.* 289:313–316 (1997), and U.S. Pat. Nos. 5,614,608 and 5,679,773). Typically, a growing polypeptide chain is covalently anchored to a solid support (or through a linker) and amino acids are added to the support-bound growing chain in a stepwise fashion. In order to prevent unwanted polymerization of the monomeric amino acid under the reaction conditions, protection of the N-terminus of the amino acid and α-amino group using blocking groups, such as tert-butyloxycarbonyl (Boc), fluorenylmethyloxycarbonyl (Fmoc) and the like, is necessary. After the monomer is coupled to the end of the polypeptide, the N-terminal protecting group is removed, and another amino acid is coupled to the chain. This cycle of coupling and deprotecting is continued for each amino acid until the desired length is reached. Photoremovable protecting group may be used to allow removal of selected portion of the solid support, via patterned irradiation, during the deprotection cycle of the solid phase synthesis (Fodor, et al., *Science* 251:767–773 (1991) and U.S. Pat. Nos. 5,143,854, 5,489,678, and 5,744,305). This selectively allows spatial control of the synthesis and the next amino acid is coupled to the irradiated areas. In addition to solid phase peptide synthesis, PCT publication WO 99/06834 describes a method for immobilizing a diverse population of antibodies to a solid support. Although the present fabrication methods are suitable for in situ synthesis, coupling of presynthesized compounds, such as polypeptides, polynucleotides, polysaccharides, or small molecules, to fabricated solid supports is within the contemplation of the instant invention. For example, presynthesized polypeptides and combinatorial libraries may be obtained commercially, such as from ArQule, Chembridge, and Combichem. These presynthesized compounds may be covalently or non-covalently attached to the array surface.

Libraries of carbohydrate compounds may also be prepared on a solid support (Ito et al., *Curr. Opin. Chem. Biol.* 2:701–708 (1998)). In solid-phase polysaccharide synthesis, elongation of a carbohydrate compounds generally consists of two steps: coupling of the glycosyl acceptor with the glycosyl donor, and selective deprotection of a temporary protecting group to liberate the free hydroxyl group that will be subjected to the next coupling with a glycosyl donor. At the final stage of polysaccharide synthesis, all protecting groups are removed. The first carbohydrate residue is typically attached to the solid support via a linker molecule and the residual hydroxyl groups are capped after each step. Stable nonclassical glycosyl donors may be utilized and they may be activated under specific conditions (Toshima et al., *Chem. Rev.* 93:1503–1531 (1993)). Sulfoxide methods developed by Kahn et al. may be used for stereoselective glycosylation of alcohol group (Yan et al., *J. Am. Chem. Soc.* 116:6953–6954 (1994)). Trichoroacetimidate, thioglycoside, n-pentenyl glycoside are also amendable to solid phase synthesis (Rademann et al., *J. Org. Chem.* 62:3650–3653 (1997), Heckel et al., *Synlett* 171–173 (1998), Nicolaou et al., *J. Am. Chem. Soc.* 119:449–450 (1998), Rodebaugh et al., *J. Org. Chem.* 62:5660–5661 (1997), Danishefsky et al., *Science* 260:1307–1309 (1993); and Zheng et al., *J. Org. Chem.* 63:1126–1130 (1998)). In addition, PCT publication 98/22487 describes methods for synthesizing very large collections of diverse thiosaccharide derivatives attached to a solid support. U.S. Pat. No. 5,846,943 and PCT publication WO 98/21221 describe novel solid support matrices having toxin-binding polysaccharide covalently attached to a solid support through a linker arm. In addition to chemical synthesis, enzymatic synthesis of polysaccharides, such as glycosyltransferase-catalyzed glycosylation, has also been proved feasible (Shuster et al., *J. Am. Chem. Soc.* 116:1135–1136 (1994), Yamada et al., *Tetrahedron Lett.* 36:9493–9496 (1995), and Blixt et al., *J. Org. Chem.* 63:2705–2710 (1998)).

Chemical synthesis of glycopeptide may also be carried out on a solid support (Meldal et al. *Curr. Opin. Chem. Biol.* 1:552–563 (1997) and Kihlberg et al., *Methods Enzymol.* 289:221–245 (1997)). Frequently, glycosylated amino acids are used as building blocks (Gururaja et al., *Lett Pept. Sci.* 3:79–88 (1996); Mcdevitt et al. *J. Am. Chem. Soc.* 118:3818–3828 (1996), and Paulsen et al., *J. Chem. Perkin Trans* 1:281–293 (1997)).

The synthesis of small organic compounds on a solid support is also well known in the art of solid phase organic synthesis (Gordon et al., *J. Med. Chem.* 37:1385–1401 (1994); Lowe, *Acc. Chem. Res.* 24:309–317 (1995), Fruchtel, *Angew. Chem. Int. Ed. Engl.* 35:17–42 (1996), Hermkens et al., *Tetrahedron* 52:4527–4554 (1996), Thompson et al., *Chem. Rev.* 96:555–600 (1996), and Andres, et al., *Curr. Opin. Chem. Biol.* 2:353–362 (1998)). In particular, PCT publication WO99/09073 describes methods of carrying out organic chemistry on solid supports comprising derivatized functionalities and methods for synthesizing compounds comprising amine group or N-containing heterocycles using functionalized solid support. U.S. Pat. No. 5,545,568 describes a general methodology for synthesizing combinatorial libraries of various nonpolymeric compounds on solid supports, such as benzodiazepine, prostaglandins, β-turn mimetics and glycerol-derived drugs. PCT publication WO 97/35198 describes methods for synthesizing spatially-dispersed and positionally-encoded combinatorial chemistry libraries of oligomers. The position of each solid support in each array determines the exact identity of the oligomers. This method is very useful for the synthesis of a peptide library and a non-peptide, low molecular weight organic compound libraries. PCT publication WO 98/46247 describes a method for immobilizing immunosupressive agent, such as cyclosporin analogs on a solid support. PCT publication WO 99/21957 discloses methods for generating libraries of organometallic catalysts on solid supports.

In addition to the use in in situ synthesis, fabricated solid supports may also be employed as platforms for simultaneously carrying out large numbers of reactions. Any suitable unimolecular or non-unimolecular reaction (two or more reactants) may be applicable to the instant invention. For example, these reactions may involve cells, viruses, nucleic acids, proteins, peptides, carbohydrates, lipids, small molecules, etc. Examples of suitable reactions include, but not limited to, sequence variation (mutations and polymorphisms) detection, gene expression monitoring, PCR reactions, enzymatic reactions, in vitro translation, drug screening, cell screening, catalyst screening, receptor binding assays, epitope mapping, protein-protein interaction studies, proteomics, etc.

EXAMPLES OF THE PREFERRED EMBODIMENTS

The following examples further illustrate the present invention. These examples are intended merely to be illustrative of the present invention and are not to be construed as being limiting.

Example 1

Preparation of Surface Tension Arrays

Glass slides (2"×2"×0.06"), purchased from Erie Scientific (Portsmouth, N.H.), were cleaned by sonication in a 2% solution of Micro 90 in Mill-Q water for 60 minutes at room temperature. The slides were then rinsed excessively with Milli-Q water and dried down with nitrogen. Next, the slides were exposed to an RF oxygen plasma (Plasmline421, Tegal, Novato, Calif.) for 60 minutes at 150 watts, 0.4 Torr, and 3.5 cc/min flow rate (Brzoska et al., *Nature* 360:719–721 (1992). The slides were further washed for 10' in a peroxysulfuric acid solution (70% $H_2SO_4$:15%$H_2O_2$, VWR, San Francisco, Calif.).

Immediately after oxygen plasma treatment, the slides were silanated with a 0.4% solution of 4-aminobutyldimethylmethoxysilane (ABS) (United Chemical Technologies, Bristol, Pa.) in anhydrous toluene (Aldrich, Milwaukee, Wis.) in a glove box under argon for 72 hours. The slides were then washed in anhydrous toluene with sonication for 15 minutes then rinsed in 95% ethanol (Aldrich) with sonication for 15 minutes. After drying each slide under nitrogen, the slides were cured for 30 minutes at 120° C. in an air oven.

Next, each slide was coated with 3.5 micron layer of a positive photoresist (Microposit 1818; Shipley, Marlborough, Mass.) by spin coating photoresist (3.4 mls) at 1250 rpm for 30 seconds. After spin coating, the photoresist was soft baked for 30 minutes at 90° C. in an air oven. Next, the slides were photomasked by placing each slide onto a chromium mask (Image Technology, Palo Alto, Calif.) that had a 19×19 spot array of round features with each feature being 1 mm in diameter with center to center spacing of 2.0 mm with the photoresist side touching the mask. The chips were then exposed to near UV irradiation with a 365 nm 500 W columnated mercury lamp (45 mW/cm$^2$, AB-M, San Jose, Calif.) for 1.0 second. After exposure, the exposed photoresist was removed by placing the slides into a solution of Microposit 350 developer (1:1 in $H_2O$, Shipley, Marlborough, Mass.) for 30 seconds with agitation and then rinsed extensively with Milli-Q water and dried under argon.

The slides were then exposed to an RF plasma (Plasmline421) 150 watts, 0.4 Torr, and 3.5 cc/min flow rate, for 6.0 minutes to remove the ABS along with residual photoresist from the photolyzed regions. Next, the slides were silated with a 0.25% solution of (tridecafluoro-1,1,2,2-tetrahydrooctyl)-1-trichlorosilane (United Chemical Technologies, Bristol, Pa.) in anhydrous toluene (Aldrich) in an argon dry box for 10 minutes at room temperature and then washed in anhydrous toluene with sonication for 15 minutes. Finally, the photoresist covering the synthesis regions was stripped by sonication in acetone (Aldrich) then by washing in NMP (Aldrich) for 60 minutes at 70° C. and washed extensively in Milli-Q $H_2O$ to remove residual photoresist.

Example 2
Linker Derivatization

All derivatizations were performed in a chip reaction chamber. Briefly, two slides were placed with their patterned surfaces facing one another. The gasket and chips were secured by four steel binder clips. Reagents were introduced via syringe through a 27-gauge needle. The gas interior was displaced through an open 27-gauge needle while reagent was being injected with the syringe. At the end of the given reaction, the reagent was removed via syringe using an open 27-gauge needle for venting. For this process, all washings between steps were done by first disassembling the reaction chamber and then rinsing each slide individually with the given solvent. Excess solvent was removed from the surface by means of a nitrogen gas stream. A fresh gasket was used for each subsequent chamber assembly and derivatization process.

For hybridization studies, prior to in situ synthesis, DMT-hexa-ethyloxy-glycol-CED phosphoramidite (Chemgenes, Waltham, Mass.) was coupled to the surface bound amines via a phosphoramidate linkage as a 1:1 solution (0.5 ml:0.5 ml) of 0.1 M linker and 0.45 M 5-ethylthiotetrazole (Glen Research, Sterling, Va.) in acetonitrile (Aldrich) for 15 minutes with mixing. After two acetonitrile washes the chips were treated with oxidizer (Glen Research) for 1 minute, washed twice with acetonitrile then the uncoupled amines were acylated for 15 minutes with acetic anhydride:pyridine (Aldrich); 1:3; v:v, for 15 minutes. Chips were stored under desiccation until use.

For cleavage and capillary electrophoresis (CE) analysis, the aminoalkylated patterned slides were initially treated with a solution of piperidine:anhydrous DMF (Aldrich); 1:5; v:v, at room temperature for 15–30 minutes then washed in anhydrous DMF. Next, the slides were placed into the reaction chamber set up as described above then a solution of 0.1 M Fmoc-HoSer(Trt)-OH (MW=583.72, Chem-Impex International, Wood Dale, Ill.) in anhydrous DMF containing 0.2 M anhydrous diusopropylethylamine (DEEA, MW=129.25, d=0.742 g/mL, Aldrich) was introduced and allowed to react for 30 minutes at room temperature. After reagent removal and disassembly, the slides were washed with DMF. Removal of the Fmoc group was done by treatment of the slides with a solution of piperidine:anhydrous DMF; 1:5; v:v, at room temperature for 15 minutes, then the slides were washed in anydrous DMF. Uncoupled amines were acylated for 30 minutes with acetic anhydride:pyridine; 1:3; v:v, for 15 minutes. Removal of the trityl protected hydroxyl group was next done for 10 minutes using a 3% TCA:DCM; w:v; solution. Finally, all chips were reacted, in a chip reaction chamber, with 1:1; v:v; 0.1M:0.45M; 2-(4,4-dimethoxytrityloxy)ethylsulfonyl] ethyl-(2-cyanoethyl)-(N,N-diisopropyl)-phosphoramidite) (Glen Research, Sterling, Va.):5-ethylthiotetrazole solution for 5 minutes in a reaction chamber. After two washes with anhydrous acetonitrile, the chips were oxidized for 1 minute then washed two times with acetonitrile. Unreacted hydroxyl groups were acylated as described above and then stored under desiccation until use.

Alternatively, linker moieties are deposited through an ink-jet printing device, which allows the deposition of different linkers on different hydrophilic sites.

Example 3
Synthesis

Drop-on-demand polynucleotide synthesis was performed on a DNA microarray synthesizer using the following reagents (all reagents were purchased from Glen Research, Sterling, Va., unless noted): phosphoramidites: pac-dA-CE phosphoramidite, Ac-dC-CE phosphoramidite, iPr-pac-dG-CE phosphoramidite, dT CE phosphoramidite (0.1M); activator: 5-ethylthio tetrazole (0.45M). Amidites and activator solutions were premixed, 1:1:v/v, in a 90% adiponitrile (Aldrich): 10% acetonitrile solution prior to synthesis. The following ancillary reagents were used: Oxidizer (0.1M iodine in THF/pyridine/water), Cap mix A (THF/2,6-lutidine/acetic anhydride), Cap mix B (10% 1-methylimidazole/THF), and 3% TCA in DCM. Parallel synthesis of individual polynucleotides was achieved by the addition of individual amidites to the hydrophillic regions of prepared surface tension arrays via custom designed piezo electric ink-jet devices (Microfab Technologies, Piano, Tex.). The jets were run at 6.67 kHz using a two step wave form which fired individual droplets of approximately 50 picoliters per drop. For the 1 mm diameter features approximately 400 drops were added to each feature per nucleotide addition. After a suitable coupling time, the uncoupled amidites were washed off of the surface by flooding with acetonitrile then removed by spinning the chip at 2000 rpm for several seconds. All other reagents were added to the surface by flooding the substrate and removed after suitable reaction times. The synthesis was done in a closed nitrogen saturated environment with a unidirectional flow of protecting gas. The synthesis cycle is summarized in Table 1.

TABLE 1

Synthesis cycle for the production of a 2" × 2" surface tension polynucleotide microarray.

| Step in Cycle | Volume (mls) | Time (seconds) |
| --- | --- | --- |
| ACN Wash | 4.2 | 5 |
| [1]Spin | | 5 |
| ACN Wash | 4.2 | 5 |
| Deblock (3% TCA in DCM) | 3.5 | 15 |
| Spin | | 5 |
| Deblock (3% TCA in DCM) | 3.5 | 15 |
| Spin | | 5 |
| ACN Wash | 4.2 | 5 |
| Spin | | 5 |
| [2]Dry down | | 10 |
| Couple Amidites | 2 × 10$^{-6}$ | 120 |
| ACN Wash | 4.2 | 5 |
| Spin | | 5 |
| Cap (Cap A:Cap B, 1:1) | 4.5 | 15 |
| Spin | | 5 |
| Oxidize | 5.5 | 15 |
| Spin | | 5 |
| Cap (Cap A:Cap B, 1:1) | 4.5 | 10 |
| Spin | | 5 |
| Re peat cycle until the desired probes are produced | | |

[1]Spin speed between successive washing steps was 2000 rpm. Washing and coupling steps were done at different locations on the chip synthesizer where there was a continuous unidirectional flow of nitrogen that was directed from the synthesis location towards the washing position. This kept the ancillary reagent vapors from interacting with the amidites. [2]A dry down was a step that was included prior to coupling to evaporate any residual ACN that may have been left on the hydrophilic regions of the array. This consisted of a high pressure nitrogen purge over the surface of the substrate.

Example 4
Cleavage and Deprotection

For arrays that were synthesized for hybridization studies, side chain protecting groups were removed by immersion of the array in an ethylenediamine:95% ethanol solution (Aldrich, Milwaukee, Wis.), 1:1, v:v for 2 hours at room temperature with shaking then washed in 95% ethanol with a squirt bottle and stored under dessication until use. For cleavage and CE analysis after synthesis of homopolymers, chips were placed in a reaction chamber as described above and 1.0 mls of aqueous ammonium hydroxide was inserted into the chamber and cleavage of the synthesis product was done for 20 minutes at room temperature with mixing. After cleavage, the cleavage product was removed from the chamber and side chain and base deprotection was done overnight at 70° C. After deprotection, the cleavage product was dried down in vacuo and resuspended in an appropriate amount of Milli-Q water.

Example 5
CE Analysis

Samples were analyzed using a Beckman P/ACE 5000 (Beckman Instruments, Palo Alto, Calif.). Sample were injected eletrokinetically (10 kV for 10 seconds) on to a 37 cm 3% T, 3% C microPAGE polyacrylamide gel filled column with 75 um I.D (J and W Scientific, Folsom, Calif., Cat. #193–3211). Separation was done at 9 kV and the separation buffer was Tris -borate pH 8.0 with 1M urea (J and W Scientific, Folsom, Calif., Cat # 590–4001). After separation, peaks were integrated using the Beckman P/ACE Station software and peak height and area were used to determine step yields by comparison of the full length product peak to the failure peaks. The average of the results from the area and height calculations was used in the determination of average step yields.

Example 6
Calculation of Average Step Yields by CE Analysis

Figure 1B:
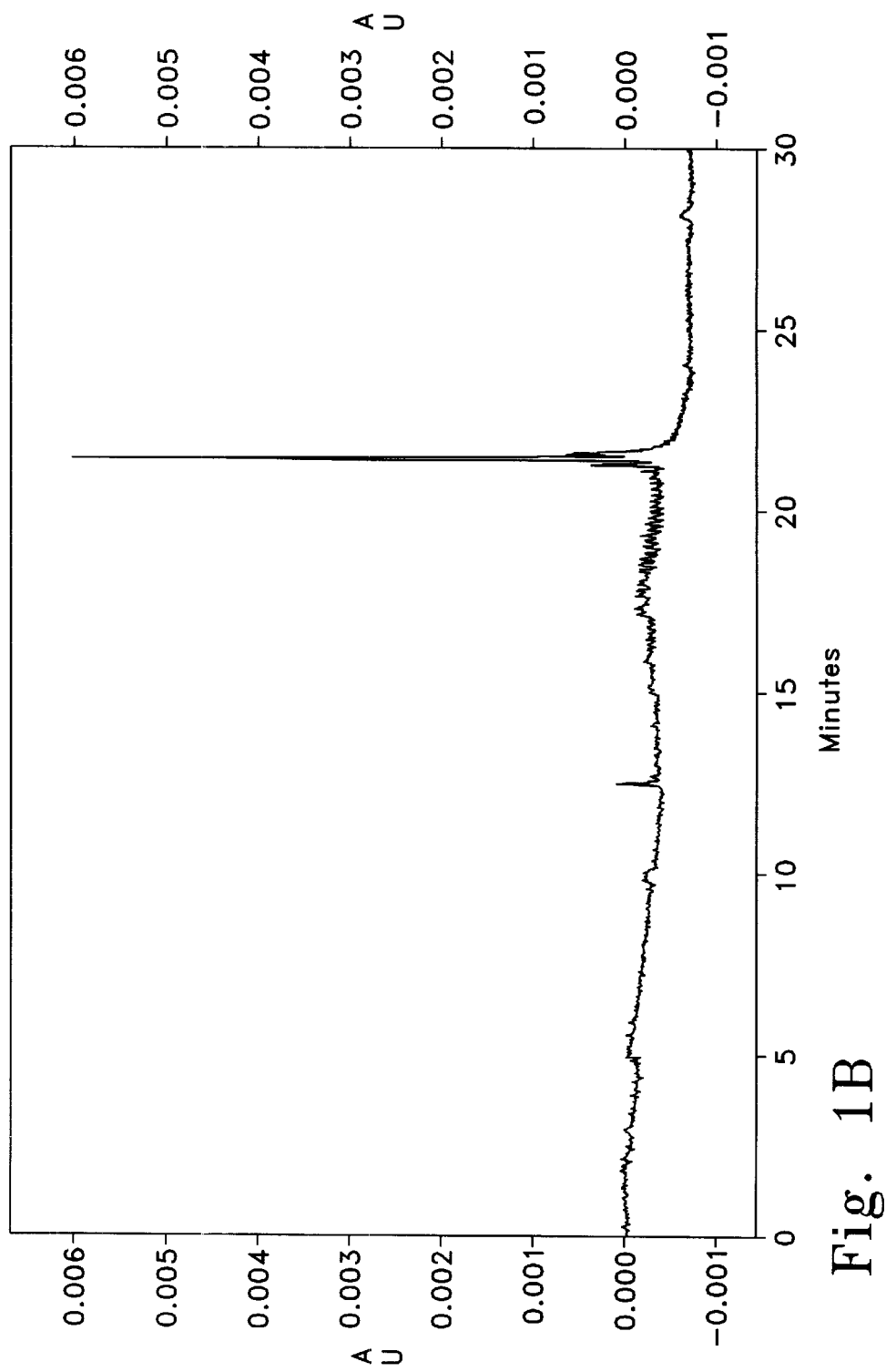
Figure 1C:
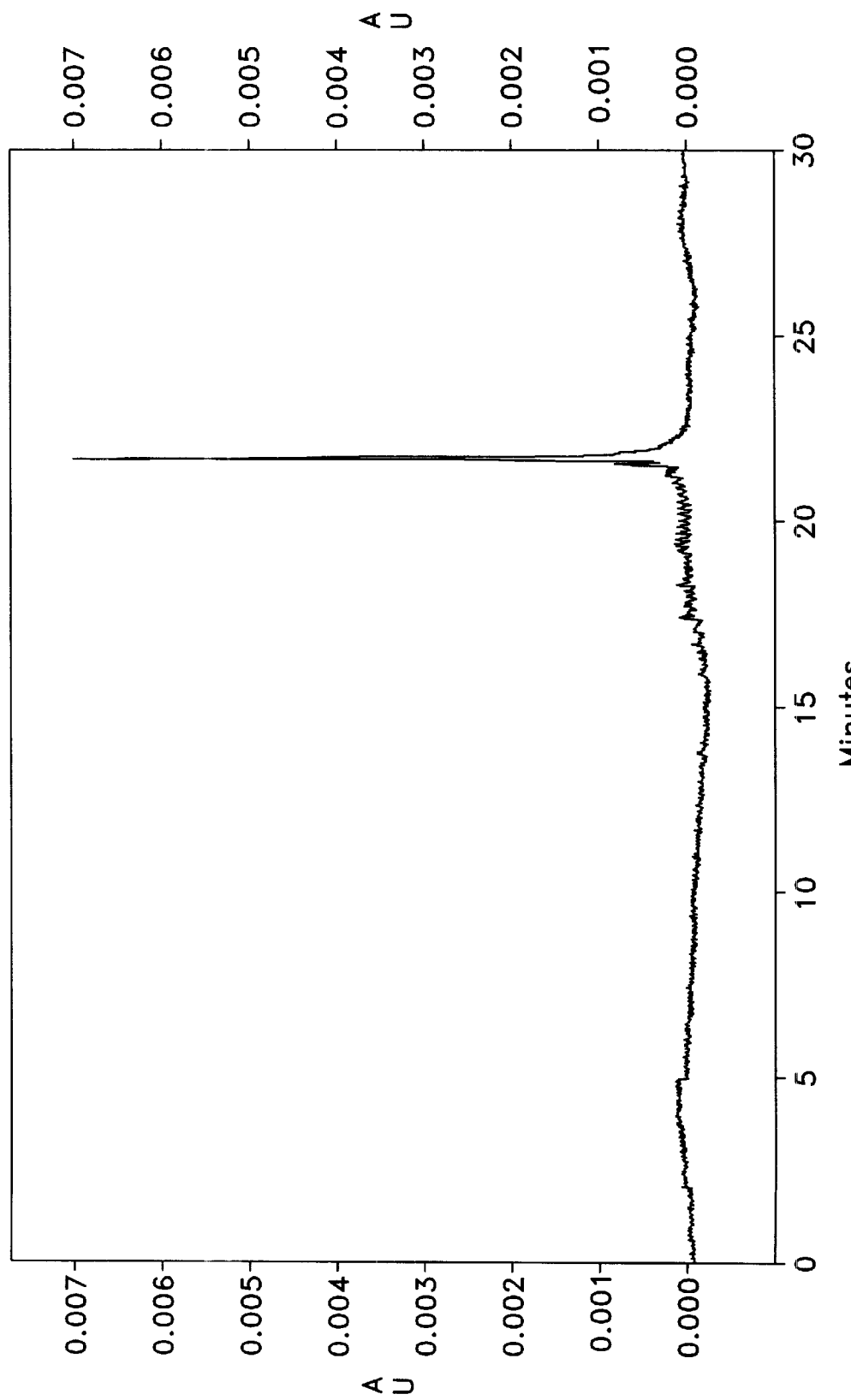

One approach to determining the step yields was CE analysis. Homopolymers (39-mers) of dT, dA, and dC were synthesized on the cleavable linker described in Example 2. The synthesis products were then cleaved off of the surface, deprotected, dried down in vacuo, and resuspended into the appropriate amount of water for CE analysis. FIG. 1A–C are the electropherograms for three 40 mer synthesis, showing the cleavage products after in situ amidite coupling of 39 dT, dA, and dC on amidites. Step yields were calculated from the failure pattern from the electropherogram of cleavage product. Peaks heights were corrected for extinction coefficient in the step yield calculation. The calculated average step yields for dA and dT amidites were about 98%.

Example 7
Calculation of Average Step Yields by Hybridization

In order to calculate the average step yields by hybridization, polynucleotides were synthesized with varying lengths of poly dT prepended to a mixed sequence 10-mer (C10, 5'-GATGCTACCG-3', SEQ. ID. No. 1) which was complimentary to the center 10 bases of a 20-mer polynucleotide (C20, 5'-GTCAAGATGCTACCGTTCAG-3', SEQ. ID. No. 2). After deprotection, the chip was placed into hybridization buffer (30 mls) in the presence of 2 nM 5'-Cy3 labeled C20 for 30 minutes at room temperature. The chip was then washed for 5 minutes in fresh buffer and scanned.

The step yields were calculated by a comparison of the fluorescence signal in an in situ synthesis site with the poly dT extensions using the following formula:

Average step =((signal with n couplings)/signal with 5 dT couplings))$^{(1/n)}$, where n=number of couplings. For each scan, the PMT (Photomultiplier Tube) setting was adjusted such that the range of signal in the C10 in situ synthesis site was within the linear range of the scanner.

The average step yields calculated from six individual experiments were about 98%.

Figure 2:
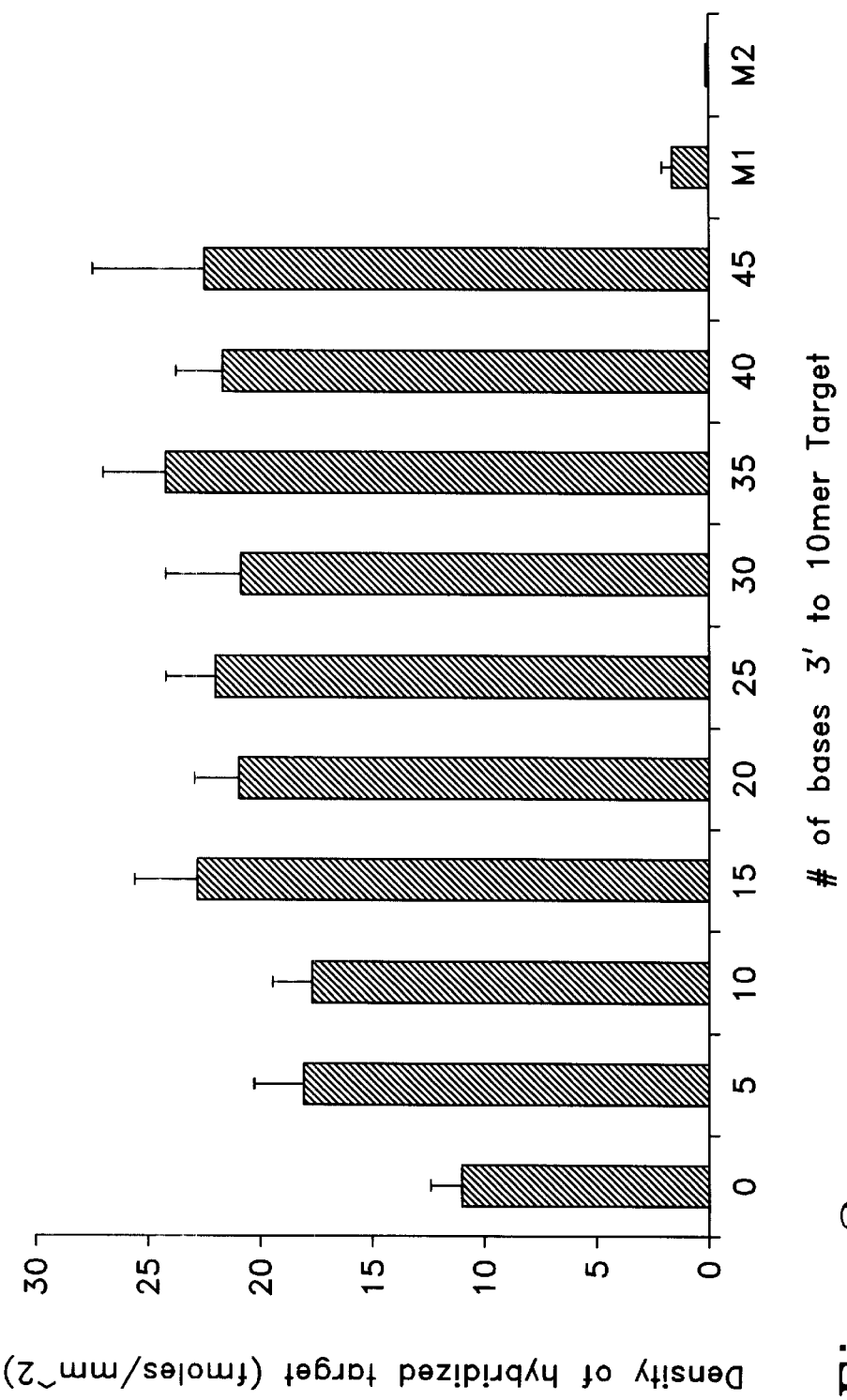
FIG. 2 illustrates step yield calculation by hybridization. Numbers on the x-axis are the numbers of nucleotides 3' to C10. Error bars are the standard deviations from 100 in situ synthesis sites.

In addition to varying lengths of poly dT prepended to C10, varying lengths of mixed sequences prepended to C10 (10mers to 55mers) were also synthesized. In particular, repeats of AGTC, such as 3'-AGTCA-5', 3'-(AGTC)$_2$AG-5' (SEQ. ID. 15 NO. 3), 3'-(AGTC)$_3$AGT-5'(SEQ. ID. NO. 4), 3'-(AGTC)$_5$-5' (SEQ. ID. NO. 5), 3'-(AGTC)$_6$A-5' (SEQ. ID. NO.6), 3'-(AGTC)$_7$AG-5' (SEQ. ID. NO. 7), 3'-(AGTC)$_8$AGT-5' (SEQ. ID. NO. 8), 3'-(AGTC)$_{10}$-5' (SEQ. ID. NO. 9), and 3'-(AGTC)$_{11}$A-5' (SEQ. ID. NO. 10), prepended to C10 were synthesized (see FIG. 2, where the number on the x-axis indicates the number of nucleotides 3' to C10). In addition, two 55-mers (M1 and M2), each with 3'-(AGTC)$_{10}$A-5' prepended to a modified C10, were also synthesized. M1 contains a single nucleotide mismatch in C10. M2 contains two nucleotide mismatches in C10. The sequence specific hybridization signal was assessed by comparing the hybridizable signal of an exact match with the hybridizable signals from mismatch polynucleotides (M1 and M2). Using the formula similar to above, the average step yields calculated were above or about 98%.

Example 8

In Situ Synthesis of Polynucleotides of 60 Nucleotides Long

Figure 3:
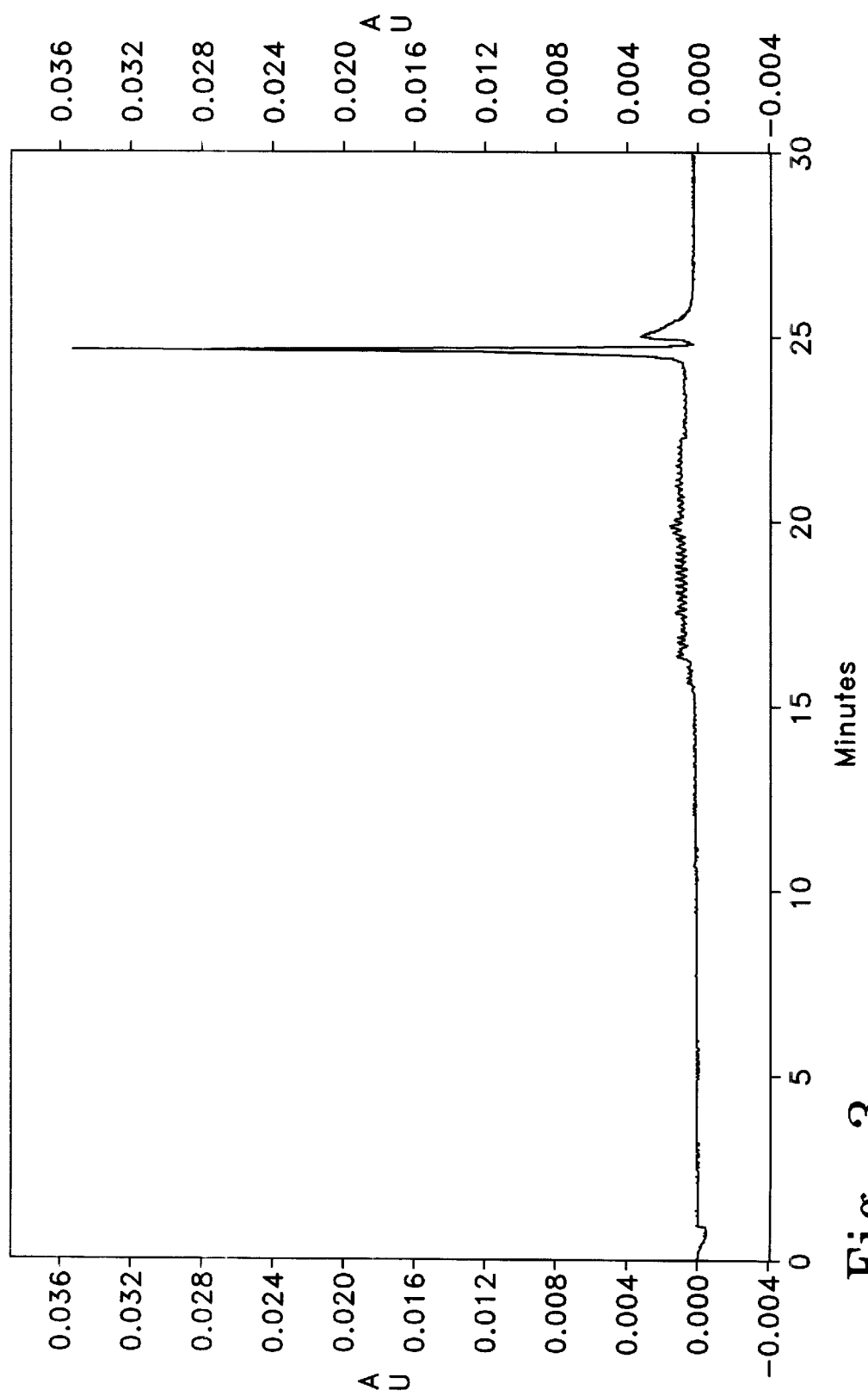
FIG. 3 illustrates the electropherogram of the cleavage products after 60 dT amidite couplings.

A dT 60-mer was synthesized on cleavable linker as described in Example 2, cleaved, deprotected, and analyzed by CE. FIG. 3 is the electropherogram for the cleavage product from a chip after 60 dT amidite couplings. The average step yield for the 60-mer was about 98%.

The above description is illustrative and not restrictive. Many variations of the invention will become apparent to those of skill in the art upon review of this disclosure. These variations may be applied without departing from the scope of the invention. The scope of the invention should, therefore, be determined not with reference to the above description, but instead should be determined with reference to the appended claims along with their full scope of equivalents.

All publications, patents, patent applications, or web sites are herein incorporated by reference in their entirety to the same extent as if each individual publication, patent, patent applications, or web site was specifically and individually indicated to be incorporated by reference in its entirety.

We claim:

1. A method for fabricating solid supports comprising the steps of:
    (a) reacting a support surface with a first reagent to form a hydrophilic surface;
    (b) coating said support surface with a photoresist substance;
    (c) exposing selected regions of said support surface to light;
    (d) developing said support surface to form a patterned exposed surface and photoresist coated surface;
    (e) reacting the exposed surface with a second reagent to form hydrophobic sites; and
    (f) removing the photoresist coat from said photoresist coated surface.

2. A method for fabricating solid supports comprising the steps of:
    (a) reacting a support surface with a first reagent to form a hydrophobic surface;
    (b) coating said support surface with a photoresist substance;
    (c) exposing selected regions of said support surface to light;
    (d) developing said support surface to form a patterned exposed surface and photoresist coated surface;
    (e) removing the photoresist coat from the photoresist coated surface; and
    (f) reacting the exposed surface with a second reagent to form hydrophilic sites.

3. The method according to claim 1 or 2 wherein said support surface has about 1–10,000 hydrophilic sites per $cm^2$.

4. The method according to claim 1 or 2 wherein said support surface as about 10–500,000 hydrophilic sites.

5. The method according to claim 1 or 2 wherein the area of each hydrophilic site is about $0.1 \times 10^{-5}$ to $0.1$ $cm^2$.

6. The method according to claim 1 or 2 wherein said support surface is a glass or silicon surface.

7. The method according to claim 1 wherein said first reagent is aminoalkylsilane or hydroxylalkylsilane.

8. The method according to claim 2 wherein said first reagent is fluoroalkylsiloxane or alkylsilane.

9. The method according to claim 1, wherein said second reagent is fluoroalkylsiloxane or alkylsilane.

10. The method according to claim 2, wherein said second reagent is aminoalkylsilane or hydroxylalkylsilane.

11. The method according to claim 1 or 2, wherein said hydrophilic sites are covalently or non-covalently attached to nucleic acids.

12. The method according to claim 1 or 2 wherein said first or second reagent is delivered using an ink-jet apparatus.

13. The method according to claim 1 or 2 wherein said first or second reagent is delivered using a piezoelectric pump.

* * * * *